(12) United States Patent
Parker

(10) Patent No.: US 6,319,490 B1
(45) Date of Patent: *Nov. 20, 2001

(54) LIQUID ORAL COMPOSITIONS COMPRISING A CALCIUM COMPOUND AND AN ACIDULANT

(75) Inventor: David Myatt Parker, Hereford (GB)

(73) Assignee: SmithKline Beecham plc, Brentford (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,471

(22) PCT Filed: Feb. 12, 1997

(86) PCT No.: PCT/EP97/00646

§ 371 Date: Aug. 19, 1998

§ 102(e) Date: Aug. 19, 1998

(87) PCT Pub. No.: WO97/30601

PCT Pub. Date: Aug. 28, 1997

(30) Foreign Application Priority Data

Feb. 20, 1996 (GB) .................................. 9603518

(51) Int. Cl.[7] .............................. A23L 2/52; A23L 2/60; A61K 33/06; A61K 7/16; A61K 7/24
(52) U.S. Cl. ............................. 424/55; 426/74; 426/590; 426/648; 426/650; 424/682
(58) Field of Search ................ 424/49.5, 49.58, 424/55, 682; 426/74, 590, 648, 650

(56) References Cited

U.S. PATENT DOCUMENTS

| | | | |
|---|---|---|---|
| 4,237,147 | * 12/1980 | Merten et al. | 426/590 |
| 4,814,177 | * 3/1989 | Walsdorf et al. | 424/464 |
| 5,028,446 | * 7/1991 | Saleeb et al. | 426/590 |
| 5,149,552 | * 9/1992 | Vidal et al. | 426/321 |
| 5,186,965 | * 2/1993 | Fox et al. | 426/74 |
| 5,194,270 | * 3/1993 | Cante et al. | 426/74 |
| 5,208,372 | * 5/1993 | Vidal et al. | 426/321 |
| 5,215,769 | * 6/1993 | Fox et al. | 426/74 |
| 5,219,602 | * 6/1993 | Saleeb et al. | 426/250 |
| 5,258,190 | * 11/1993 | Cante et al. | 426/74 |
| 5,270,297 | * 12/1993 | Paul et al. | 426/810 |
| 5,424,082 | * 6/1995 | Dake et al. | 426/72 |
| 5,445,837 | * 8/1995 | Burkes et al. | 426/74 |
| 5,468,506 | * 11/1995 | Andon | 426/74 |
| 5,474,793 | * 12/1995 | Meyer et al. | 426/74 |
| 5,500,232 | * 3/1996 | Keating | 426/74 |
| 5,597,595 | * 1/1997 | DeWille et al. | 426/74 |
| 5,690,975 | * 11/1997 | Akahoshi et al. | 426/74 |
| 5,817,351 | * 10/1998 | DeWille et al. | 426/74 |
| 5,939,117 | * 8/1999 | Chen et al. | 426/267 |

FOREIGN PATENT DOCUMENTS

| | | |
|---|---|---|
| 0227174 | 7/1987 | (EP) . |
| 244903A1 | * 11/1987 | (EP) . |
| 301653A1 | * 2/1989 | (EP) . |
| 587972A1 | * 3/1994 | (EP) . |
| 0634110 | 1/1995 | (EP) . |
| 713652A1 | * 5/1996 | (EP) . |
| 1516525 | 7/1978 | (GB) . |
| WO 88/03762 | 6/1988 | (WO) . |
| 88/03762A1 | * 6/1988 | (WO) . |
| 92/05711A1 | * 4/1992 | (WO) . |
| 97/21356A1 | * 6/1997 | (WO) . |

OTHER PUBLICATIONS

Lussi et al (I) Caries Res. 27(5):387–393 The Influence of Different Factors on In Vitro Enamel Erosion, 1993.*
Lussi et al (II) Caries Res. 29(5):349–354 Prediction of the Erosive Potential of Some Beverages, 1995.*
Rugg–Gunn et al., "Comparison of Erosion of Dental Enamel by Four Drinks Using an Intra–Oral Applicance", Caries Research, 1998(32), pp. 337–343.
Hughes et al., "Development and evaluation of a low erosive blackcurrant juice drink 3. Final drink and concentrate, formulae comparisons in situ and overview of the concept.", Journal of Dentistry, 1999(27), pp. 345–350.

* cited by examiner

Primary Examiner—Shep K. Rose
(74) Attorney, Agent, or Firm—Dara L. Dinner; Stephen Venetianer; Charles M. Kinzig

(57) ABSTRACT

Acidic oral compositions having reduced tooth erosion characteristics, especially acid beverages such as fruit juice drink concentrates, or oral healthcare products such as mouthwashes, are prepared by adding a calcium compound to the acid composition so that the mol ratio of calcium to acid ranges from 0.3 to 0.8, and the pH of the composition, if necessary after adjustment with an alkali, is from 3.5 to 4.5.

36 Claims, No Drawings

LIQUID ORAL COMPOSITIONS COMPRISING A CALCIUM COMPOUND AND AN ACIDULANT

The present invention relates to compositions for oral use, such as acidic beverages and oral healthcare compositions, and to the use of calcium in such compositions to alleviate or prevent the tooth damage associated with the consumption of acid. In particular, the present invention alleviates palatability problems associated with calcium addition to beverages.

It is thought that erosion of teeth is caused inter alia by acidic foodstuffs leaching out calcium from the teeth faster than it can be replaced by normal remineralisation processes. When a product such as a beverage is prepared in accordance with this invention, and introduced into the oral cavity for consumption or healthcare purposes, the dissolution or removal of calcium and phosphate from teeth by chemical processes is significantly reduced.

Calcium is the most abundant mineral in the body. The vast majority of calcium is deposited in the bones and teeth but the mineral is also essential for other bodily functions such as the regulation of nerve function, the contraction of muscles and clotting of blood. Calcium is a common constituent of beverages being derived from fruit ingredients and from hard water when this is used in beverage production without prior softening. Values for the concentration of calcium occurring in this way are typically in the range 0.005–0.02% w/w. Interest in the general nutritional benefits of diet fortification by calcium ion has led to a search for practical ways to incorporate this ion in beverages at higher levels from 0.02% w/w to 2% w/w. The use of calcium as a supplement for beverages has been described in WO88/03762.

It is well known that the addition of malic acid will help maintain the solubility of calcium in calcium fortified beverages therefore minimizing losses due to precipitation. This is because of the formation of a soluble complex "calcium citrate malate". On the other hand, Lussi et al (1995, Caries Res 29, 349–354) have associated the titratable acidity of a beverage with its erosive potential, the greater the concentration of acid in the beverage the more damaging to teeth it became.

In PCT U.S. 91/07117 there is disclosed a method for preventing the erosion of tooth enamel by consuming an acid beverage (having a pH of less than 5.5) comprising from 0.02% to 0.15% of calcium in the form of a calcium citrate malate complex having a molar ratio of citrate to malate of 1:0.5 to 1:4.5. In the calcium citrate malate complexes the molar ratio of total moles calcium:total moles citrate:total moles malate may be from about 2:1:1 to about 6:3:4. A preferred complex for beverages has the molar ratio 4:2:3.

We have found that inclusion of high levels of calcium in beverages gives palatability problems. The present invention is based on the discovers that effective reduction of tooth erosion in acidic oral compositions can be achieved with lower amounts of calcium relative to the acidulant when the pH of the composition is also controlled.

In one aspect, the present invention provides a liquid composition for oral use containing a calcium compound and an acidulant characterised in that calcium is present in the range of 0.3 to 0.8 mol per mol of acid and that the amount of calcium and acidulant in the composition is selected so that the pH of the composition is from 3.5 to 4.5.

In another aspect, the present invention provides the use of calcium as a tooth erosion inhibitor in an acidic liquid composition for oral use by adding a calcium compound to the composition so that calcium is present in the range of 0.3 to 0.8 mol per mol of acid, the amount of calcium and acidulant in the composition being selected so that the pH of the composition is from 3.5 to 4.5.

In a further aspect, the present invention provides a method of reducing the tooth erosion properties of an acidic oral composition which comprises adding a calcium compound to the acidic liquid oral composition so that calcium is present in the range of 0.3 to 0.8 mol per mol of acid, and if necessary or desired adjusting the pH by addition of an alkali so that the pH of the composition is from 3.5 to 4.5.

In a still further aspect, the present invention provides a process for preparing a composition of this invention which comprises adding a calcium compound to an acidic liquid oral composition so that calcium is present in the range of 0.3 to 0.8 mol per mol of acid, and if necessary or desired adjusting the pH by addition of an alkali so that the pH of the composition is from 3.5 to 4.5.

The present invention is applicable to aqueous acidic substances for oral consumption such as acidic beverages, fruit juices, ciders, wines, vinegars and pickles and diverse acidic dairy products and also to other liquid substances to be taken orally such as acidic mouth washes and medicines.

Practice of the present invention does not cause taste defects in beverages. Although the increase in pH of a beverage to around pH 4 would be expected to reduce the sharpness in taste provided by the acidulant, surprisingly the inclusion of calcium in accordance with this invention mitigates this.

A further advantage arises from the use of low levels of calcium in accordance with this invention in the form of an alkaline salt. The buffering capacity of the formulation is reduced by, partial neutralization of the acid, which allows saliva to neutralise residues in the mouth more rapidly.

The absolute concentration of calcium used in the present invention is not critical as this will vary according to the nature and concentration of the acids present. The acid solution may contain organic and/or inorganic acids and may be supplemented with vitamins such as ascorbic acid. In a concentrated beverage, to be diluted with up to five parts of water prior to consumption, the calcium concentration may vary from 0.001 mol. per liter to more than 0.05 mol. per liter. In a ready to drink beverage the calcium ion concentration may vary from 0.0002 mol. per liter to more than 0.01 mol. per liter.

The calcium may be added as any convenient salt such as calcium carbonate, calcium hydroxide, calcium citrate, calcium malate, calcium lactate, calcium chloride, calcium glycerophosphate or calcium formate or any other salt to minimize any adverse flavour contribution to the composition.

The invention may be carried out by mixing the acid (e.g. citric acid) with its corresponding calcium salt (e.g. calcium citrate) or another calcium salt. It may be advantageous to mix the acid with an alkaline calcium salt such as calcium carbonate or calcium hydroxide thereby minimizing the concentration of acid applied to the formulation. The acid can also be mixed with inorganic calcium salts such as calcium chloride.

The molar ratio of calcium to acid may be 0.3–0.75, more typically 0.3–0.65, preferably 0.3–0.55. Most preferably the molar ratio is at least 0.4, and a value of about 0.5 has been found to be especially effective.

The pH of the formulation may be adjusted to the desired range by the addition of the calcium compound to the appropriate proportion relative to the acid. If necessary, depending on the acid present, the pH may be further adjusted by the application of an alkali e.g. sodium hydroxide or a suitable salt for example sodium citrate, sodium malate or sodium lactate.

The pH of the composition is preferably not more than 4, most preferably from 3.7 to 3.9. Compositions with a pH of about 3.8 have been found to be especially effective.

Typical citric or malic acid concentration in a concentrated fruit beverage would be in the range 0.1% w/w to 4% w/w. In a ready to drink beverage, acid concentrations are typically in the range 0.01% w/w to 1% w/w. Other potable acids conventional for beverages may also be used, such as lactic acid. Mixtures of potable acids may be used.

In a preferred embodiment, the acid composition is a drink concentrate prepared from a natural fruit juice, such as black currant juice, for example a flavoured syrup concentrate. The calcium may be added in a suitable form either to the concentrate, especially when the beverage is sold to the consumer as a concentrate for dilution before drinking, or when diluting the syrup concentrate for preparation of a "ready to drink" diluted concentrate. Preferably the product contains reduced levels of sugar or carbohydrate or is of low calorie type containing intense sweeteners.

The oral composition may contain magnesium or other ions as adjuncts for remineralisation. It may also contain an effective amount of malic acid or potable salts thereof to maintain the solubility of the calcium so as to prevent or minimize the precipitation of insoluble calcium salts. Added malic acid may provide as little as 10% of the total acidity of the beverage, the remainder of the acidity being provided by other preferably naturally present, acids such as citric acid, or by ascorbic acid.

The invention may be applied in a variety of beverages such as concentrates, still fruit drinks, or carbonated soft drinks and in particular to health drinks such as black currant juice drinks or vitamin added beverages. The invention is advantageously applied to drinks containing natural or added citric acid. The beverages may be unsweetened or sweetened with sugar or intense sweeteners such as saccharine, aspartyl phenyl alanyl methyl ester, or other sweeteners known in the art. The beverages may also contain other conventional additives such as sodium benzoate, sorbic acid, sodium metabisulfite, ascorbic acid, flavourings, colourings and carbon dioxide.

The beverages may be prepared by mixing the ingredients according to conventional methods. The solid ingredients may be dissolved in water or in hot water if required prior to addition to the other components. Typically drinks are pasteurised prior to filling in bottles or cans or other packs or are "in-pack pasteurised" after filling. The invention is illustrated by the following Examples:

EXAMPLE 1

A concentrated beverage product, for dilution with five parts of water prior to consumption was prepared by mixing the ingredients as follows. The calcium carbonate was added to the other ingredients as a final addition.

| | | |
|---|---|---|
| Blackcurrant juice concentrate | SG 1.27 | 84 liter |
| Aspartyl phenyl alanyl methyl ester* | | 1.15 Kg |
| Acesulfame K | | 1.8 Kg |
| Ascorbic acid | | 0.8 Kg |
| Sodium benzoate | | 0.325 Kg |
| Sodium metabisulfite | | 0.145 Kg |
| Blackcurrant flavouring | | 0.3 liter |
| Water | up to final volume | 1000 liter |
| Calcium carbonate | | 4.2 Kg |

*sold as Aspartame (RTM)

The mol ratio of calcium: acid is 0.5

The concentrate is adjusted to pH 3.7 with sodium hydroxide solution. On dilution of the concentrate with five parts water (to drinking strength), the pH of the composition is typically found to be 3.85.

In-vitro planometry tests were performed in which flat dental enamel sections were exposed to test solutions at a temperature of 37° C. for 30 minutes. Erosive potential was evaluated by physical measurement of the depth of enamel lost during the procedure. Whereas a control formulation comprising 14 mM citric acid, pH 3.2 resulted in a loss of 4 microns of enamel and a further control formulation of 14 mM citric acid, pH 3.85, removed 1.8 microns, a test formulation with adjusted pH and added calcium comprising 14 mM citric acid, 7 mM calcium, pH 3.85 removed only 0.17 microns of enamel, demonstrating the utility of the invention.

EXAMPLE 2

A ready to drink beverage was prepared by mixing ingredients as follows:

| Ingredients | | % w/w |
|---|---|---|
| Sugar | | 10 |
| Sodium benzoate | | 0.01 |
| Orange juice | | 5.04 |
| Ascorbic acid | | 0.03 |
| Citric acid monohydrate | | 0.15 |
| Flavouring | | 0.005 |
| Colouring | | 0.004 |
| Water | by difference | 86 |
| Calcium carbonate | | 0.048 |
| Sodium hydroxide | sufficient to adjust to pH | 3.9 |
| Carbon dioxide | | 0.48 |

In this beverage the mol ratio of calcium: acid is 0.46 (orange juice is typically 1% w/w citric acid)

EXAMPLE 3

A ready to drink beverage was prepared by mixing ingredients as follows:

| Ingredients | | % w/w |
|---|---|---|
| Sugar | | 8 |
| Sodium benzoate | | 0.01 |
| Apple juice | | 10 |
| Ascorbic acid | | 0.03 |
| Malic acid | | 0.15 |
| Flavouring | | 0.005 |
| Colouring | | 0.004 |
| Water | by difference | 82 |
| Calcium carbonate | | 0.093 |
| Sodium hydroxide | sufficient to adjust to pH | 3.9. |

In this beverage the mol ratio of calcium : acid is 0.74 (apple juice is typically 0.6% w/w malic acid)

EXAMPLE 4

In vivo Study

A beverage was produced by mixing ingredients as follows:

| | |
|---|---|
| Blackcurrant concentrate | 16.78 liters |
| Aspartyl phenyl alanyl methyl ester | 0.54 kg |
| Acesulfame K | 0.11 kg |
| Ascorbic acid | 0.45 kg |
| Flavouring | 0.55 liters |
| Calcium hydroxide | 0.52 kg |
| Water | to 1000.00 liters |

The calcium hydroxide was added as a slurry with a portion of the water as a final addition and was sufficient to produce a beverage containing calcium in a molar ratio of 0.5:1 calcium to citric acid. The resultant beverage had a pH of 3.8. The batch was flash pasteurised and packed into 250 ml "Tetra-Brik" containers.

In this study, loss of human enamel was compared between three beverages: the above example, an orange juice as a positive control (pH 3.8) and water as negative control.

Twelve volunteers participated in the study in a three-treatment Latin square crossover design. Each study period consisted of three weeks each consisting of five weekdays. In each study period, a section of enamel from an extracted healthy tooth was worn in an appliance for seven hours each weekday. On four occasions during this period 250 ml of the test beverage was sipped gradually, under supervision, during a period of ten minutes. The subjects were permitted to remove the appliance to consume a mid-day meal but were not allowed to consume foods or other beverages whilst the appliance was in place. The enamel specimen underwent measurement by planometry (the principles of the method have been described by Davis and Winter (1977) British Dental Journal 143, 116–119) at the start of the treatment period and at the end of each treatment week. All readings were performed in duplicate. After a washout period, each subject then commenced the next treatment period with a fresh enamel specimen. The results are given in the following table and represent microns of enamel lost by the given treatment after the given exposure time and are the means found for the twelve subjects.

| | 5 days | 10 days | 15 days |
|---|---|---|---|
| water | 0.098 | 0.153 | 0.166 |
| blackcurrant | 0.341 | 0.376 | 0.407 |
| orange juice | 0.911 | 1.459 | 2.543 |

The results demonstrate that the black currant formulation was found to be minimally erosive, barely more erosive than water, and highly significantly less erosive than orange juice.

EXAMPLE 5

In-vitro Study supplemented with either 0.0, 0.5, 1.5, 2.5, 5.0, 7.5 10 or 15 mM calcium in the form of calcium hydroxide and the pH was adjusted to 3.5 or 3.8 using 1.0 M sodium hydroxide. Samples of residual citric acid were collected after every 5 min exposure of the teeth and these were frozen at $-4°$ C., prior to phosphorus analysis by the method of Chen et al (1956) Analytical Chemistry, Vol.28, p1956–8.

The results are illustrated below

| calcium | mol ratio | Mean amount Phosphorus liberated ($\mu$g) ± 1 SD | |
|---|---|---|---|
| (mM) | calcium:acid | pH 3.5 | pH 3.8 |
| 0 | 0.00 | 1.41 ± 0.11 | 1.26 ± 0.17 |
| 0.5 | 0.03 | 1.25 ± 0.14 | 1.02 ± 0.09 |
| 1.5 | 0.10 | 1.07 ± 0.15 | 0.83 ± 0.12 |
| 2.5 | 0.17 | 1.22 ± 0.14 | 0.63 ± 0.13 |
| 5 | 0.35 | 0.79 ± 0.06 | 0.46 ± 0.13 |
| 7.5 | 0.52 | 0.72 ± 0.1 | 0.32 ± 0.10 |
| 10 | 0.70 | 0.46 ± 0.13 | 0.24 ± 0.11 |
| 15 | 1.05 | 0.3 ± 0.10 | 0.14 ± 0.07 |

This experiment clearly illustrates that addition of calcium to a 0.3% citric acid solution reduces its erosive potential. The effect is greatest up to a calcium to acid molar ratio of about 0.5 (approximately 7.5 mM calcium). No justifiable decrease in erosive potential can be achieved by increasing the calcium: acid molar ratio much beyond this point.

EXAMPLE 6

A flavoured concentrate was prepared by mixing the following ingredients together with stirring. The calcium hydroxide was added last as a slurry in cold water and the volume adjusted to 1000 L with water.

| Ingredient | Unit | Quantity |
|---|---|---|
| Blackcurrant Concentrate | L | 67.1 |
| Sweetener | Kg | 3.33 |
| Ascorbic Acid | Kg | 2.28 |
| Preservatives | Kg | .0.45 |
| Flavouring | L | 1.2 |
| Calcium Hydroxide | kg | 2.96 |
| Water to 1000 liters | | |

The beverage concentrate was flash pasteurised at 93° C. for 42 seconds and filled into 600ml bottles. The molar ratio of calcium to citric acid was 0.4 and the final pH was 3.7.

On dilution with five parts water to drinking strength the pH of the composition was found to be 3.85 and the flavour of the drink was described as being typical fruity blackcurrant.

The beverage concentrate was tested for storage stability both at ambient and at 30° C. After a period of 9 months no precipitation of insoluble calcium was observed.

EXAMPLE 7

In vivo Study

A beverage was produced by mixing ingredients as follows:

| | |
|---|---|
| Blackcurrant concentrate | 10.07 liters |
| Aspartyl phenyl alanyl methyl ester | 0.21 kg |
| Acesulfame K | 0.07 kg |
| Ascorbic acid | 0.27 kg |
| Lactic acid 80% w/w | 0.66 liters |
| Potassium sorbate | 0.1 kg |

| -continued | |
|---|---|
| Sodium metabisulfite | 0.02 kg |
| Flavouring | 0.56 liters |
| Calcium hydroxide | 0.52 kg |
| Water | to 600.00 liters |

The calcium hydroxide was added as a slurry with a portion of the water as a final addition and was sufficient to produce a beverage containing calcium in a molar ratio of 0.45:1 calcium to citric acid/lactic acid. The resultant beverage had a pH of 3.85. The batch was packed in 250ml containers and "in-pack" pasteurised.

In this study, loss of human enamel was compared between four beverages: the above example, a commercially available blackcurrant fruit drink with a pH of 3.0 and no added calcium an orange juice as a positive control (pH 3.9) and water as negative control.

Twelve volunteers participated in the study. Each study period consisted of three weeks each consisting of five weekdays. In each study period, a section of enamel from an extracted healthy tooth was worn in an appliance for seven hours each weekday. On four occasions during this period 250 ml of the test beverage was sipped gradually, under supervision, during a period of ten minutes. The subjects were permitted to remove the appliance to consume a mid day meal but were not allowed to consume foods or other beverages whilst the appliance was in place. The enamel specimen undervent measurement by planometry (the principles of the method have been described by Davis and Winter (1977) British Dental Journal 143, 116–119) at the start of the treatment period and at the end of each treatment week. All readings were performed in duplicate. After a washout period, each subject then commenced the next treatment period with a fresh enamel specimen.

The results are given in the following table and represent microns of enamel lost by the given treatment after the given exposure time.

| | 15 days |
|---|---|
| water | 0.11 |
| blackcurrant | 0.39 |
| commercial blackcurrant | 1.44 |
| orange juice | 1.29 |

The results demonstrate that the blackcurrant formulation was found to be minimally erosive, barely more erosive than water, and highly significantly less erosive than orange juice or the commercial blackcurrant drink.

EXAMPLE 8

A cola concentrate was prepared by mixing the following ingredients together

| orthophosphoric acid SG 1.585 | 41 l |
|---|---|
| citric acid | 120 Kg |
| caffeine BP | 5.3 Kg |
| cola emulsion | 29.25 l |
| caramel double strength | 125 l |
| water to | 400 l |

A cola syrup with a throw of 1+5 was then prepared by mixing the following ingredients together

| Aspartyl phenyl alanyl methyl ester | 1.8 Kg |
|---|---|
| soluble saccharin | 500 g |
| cola concentrate | 25 l |
| cola booster | 600 mls |
| calcium hydroxide | 3.108 Kg |
| water to | 1000 l |

The calcium hydroxide was added as a slurry with a portion of the water as a final addition and the cola syrup was then diluted with carbonated water, canned and in pack pasteurised to produce a finished product with a pH of 3.5 and a calcium to acid molar ratio of 0.6.

EXAMPLE 9

A mouthwash was prepared by mixing the following ingredients:

| | % W/W |
|---|---|
| ethanol 96% BP | 8 |
| soluble Saccharin | 0.06 |
| cetylpyridinium chloride | 0.05 |
| Tego Betain CK-KB5 | 0.2 |
| flavouring | 0.12 |
| sodium acetate trihydrate | 0.05 |
| acetic acid 80% | 0.1575 |
| calcium chloride dihydrate | 0.123 |
| deionised water | 91.24 |

The ethanol, cetvipyridinium chloride. Tego Betain CK-KB5 (Trade Mark for a cocamido propyl betaine) and flavouring were mixed together to form a clear solution. In a separate container the remainder of the ingredients were mixed together. The ethanolic solution was then added to the aqueous solution to produce a mouthwash with a pH of 4.5 and a calcium to acid molar ratio of 0.4.

EXAMPLE 10

A ready to drink beverage was prepared by mixing ingredients as follows:

| Ingredients | | % w/v |
|---|---|---|
| Sodium benzoate | | 0.01 |
| Malic acid | | 0.30 |
| Flavouring | | 0.1 |
| Artificial sweetener | | 0.05 |
| Water | by difference | 99.5 |
| Calcium hydroxide | | 0.083 |

The resultant pH of the composition is typically found to be 3.85 and has a calcium to acid molar ratio of 0.5.

In vitro planometry tests were performed in which flat dental enamel sections were exposed to test solutions at a temperature of 37° C. for 30 minutes. Erosive potential was evaluated by physical measurement of the depth of enamel lost during the procedure. Whereas a control formulation lacking the addition of calcium hydroxide gave a pH of 2.5 and resulted in a loss of 8.1 microns of enamel and a further control formulation in which the pH of the beverage had been increased to pH 3.85 with sodium hydroxide removed 1.65 microns, the composition detailed above removed only 0.6 microns of enamel, demonstrating its utility in reducing tooth erosion.

What is claimed is:

1. A method of reducing the tooth erosion properties of an acidic oral composition used for oral administration, comprising adding calcium to the acidic liquid oral composition wherein the calcium is present in the range of 0.3 to 0.8 mol per mol of acid and the pH of the composition is from 3.5 to 4.5; and adjusting the pH, if necessary or desired, by addition of an alkali such that the pH of the resulting composition is in the range of 3.5 to 4.5; subject to the proviso that if the composition is a fruit-containing liquid having a fruit content of 25 to 100% by weight and an acid content of at least 5 g/liter (calculated as tartaric acid), then it contains less than 2 g/liter of dissolved calcium phosphate.

2. A method of reducing the tooth erosion properties of an acidic oral composition used for oral administration, comprising adding calcium to the acidic liquid oral composition wherein the calcium is present in the range of 0.3 to 0.55 mol per mol of acid and the pH of the composition is from 3.5 to 4.5, and adjusting the pH, if necessary or desired, by addition of an alkali such that the pH of the resulting composition is in the range of 3.5 to 4.5.

3. A method of reducing tooth erosion in a human caused by acid in an orally administered composition which method comprises orally administering to said human a liquid composition comprising a calcium compound and an acidulant, wherein the calcium is present in the range 0.3 to 0.8 mol per mol of acid and the pH of the composition is from 3.5 to 4.5; subject to the proviso that if the composition is a fruit-containing liquid having a fruit content of 25 to 100% by weight and an acid content of at least 5 g/liter (calculated as tartaric acid), then it contains less than 2 g/liter of dissolved calcium phosphate.

4. A method of reducing tooth erosion in a human caused by acid in an orally administered composition which method comprises orally administering to said human a liquid composition comprising a calcium compound and an acidulant, wherein the calcium is present in the range 0.3 to 0.55 mol per mol of acid and the pH of the composition is from 3.5 to 4.5.

5. The method as claimed in claim 3 in which the calcium is present in an amount of at least 0.4 mol per mol of acid.

6. The method as claimed in claim 3 in which the pH of the composition is not more than 4.

7. The method as claimed in claim 3 in which the pH of the composition is from 3.7 to 3.9.

8. The method as claimed in claim 3 in which the acidic liquid composition is a beverage.

9. The method as claimed in claim 8 in which the beverage is a still fruit drink, a carbonated soft drink, or a health drink.

10. The method as claimed in claim 3 in which the acidic liquid composition is a drink concentrate for the preparation of a beverage.

11. The method as claimed in claim 3 in which the acid is citric acid or malic acid or lactic acid or mixtures thereof.

12. The method as claimed in claim 3 in which the calcium compound is calcium carbonate, calcium hydroxide, calcium citrate, calcium malate, calcium lactate, calcium chloride, calcium glycerophosphate or calcium formate.

13. The method as claimed in claim 1 in which the acid is citric acid or malic acid or lactic acid or mixtures thereof.

14. The method as claimed in claim 1 in which the calcium compound is calcium carbonate, calcium hydroxide, calcium citrate, calcium malate, calcium lactate, calcium chloride, calcium glycerophosphate or calcium formate.

15. The method as claimed in claim 2 in which the calcium is present in an amount of at least 0.4 mol per mol of acid.

16. The method as claimed in claim 2 in which the pH of the composition is not more than 4.

17. The method as claimed in claim 2 in which the pH of the composition is from 3.7 to 3.9.

18. The method as claimed in claim 2 in which the acidic liquid composition is a beverage.

19. The method as claimed in claim 18 in which the beverage is a still fruit drink, a carbonated soft drink, or a health drink.

20. The method as claimed in claim 2 in which the acidic liquid composition is a drink concentrate for the preparation of a beverage.

21. The method as claimed in claim 2 in which the acid is citric acid or malic acid or lactic acid or mixtures thereof.

22. The method as claimed in claim 2 in which the calcium compound is calcium carbonate, calcium hydroxide, calcium citrate, calcium malate, calcium lactate, calcium chloride, calcium glycerophosphate or calcium formate.

23. The method as claimed in claim 4 in which the calcium is present in an amount of at least 0.4 mol per mol of acid.

24. The method as claimed in claim 4 in which the pH of the composition is not more than 4.

25. The method as claimed in claim 4 in which the pH of the composition is from 3.7 to 3.9.

26. The method as claimed in claim 4 in which the acidic liquid composition is a beverage.

27. The method as claimed in claim 26 in which the beverage is a still fruit drink, a carbonated soft drink, or a health drink.

28. The method as claimed in claim 4 in which the acidic liquid composition is a drink concentrate for the preparation of a beverage.

29. The method as claimed in claim 4 in which the acid is citric acid or malic acid or lactic acid or mixtures thereof.

30. The method as claimed in claim 4 in which the calcium compound is calcium carbonate, calcium hydroxide, calcium citrate, calcium malate, calcium lactate, calcium chloride, calcium glycerophosphate or calcium formate.

31. The method as claimed in claim 1 in which the calcium is present in an amount of at least 0.4 mol per mol of acid.

32. The method as claimed in claim 1 in which the pH of the composition is not more than 4.

33. The method as claimed in claim 1 in which the pH of the composition is from 3.7 to 3.9.

34. The method as claimed in claim 1 in which the acidic liquid composition is a beverage.

35. The method as claimed in claim 34 in which the beverage is a still fruit drink, a carbonated soft drink, or a health drink.

36. The method as claimed in claim 1 in which the acidic liquid composition is a drink concentrate for the preparation of a beverage.

* * * * *